(12) United States Patent
Jia et al.

(10) Patent No.: US 11,713,302 B2
(45) Date of Patent: Aug. 1, 2023

(54) SULFONAMIDE BENZAMIDE DERIVATIVE AND PREPARATION METHOD AND APPLICATION THEREOF

(71) Applicant: WEIFANG MEDICAL UNIVERSITY, Weifang (CN)

(72) Inventors: Haiyong Jia, Weifang (CN); Chuanju Li, Weifang (CN); Lei Zhang, Weifang (CN); Linyue Liu, Weifang (CN); Mei Wang, Weifang (CN); Xin Li, Weifang (CN); Xianghui Han, Weifang (CN)

(73) Assignee: WEIFANG MEDICAL UNIVERSITY, Weifang (CN)

( * ) Notice: Subject to any disclaimer, the term of this patent is extended or adjusted under 35 U.S.C. 154(b) by 0 days.

(21) Appl. No.: 17/663,153

(22) Filed: May 12, 2022

(65) Prior Publication Data

US 2022/0388975 A1    Dec. 8, 2022

(30) Foreign Application Priority Data

May 18, 2021    (CN) .......................... 202110542168.5

(51) Int. Cl.
*C07D 319/16* (2006.01)
*C07D 405/12* (2006.01)
*C07D 413/12* (2006.01)

(52) U.S. Cl.
CPC ......... *C07D 319/16* (2013.01); *C07D 405/12* (2013.01); *C07D 413/12* (2013.01)

(58) Field of Classification Search
CPC .................................................. C07D 319/16
See application file for complete search history.

(56) References Cited

U.S. PATENT DOCUMENTS 9,085,517 B2 *   7/2015   Rawson ............... C07D 213/64

* cited by examiner

*Primary Examiner* — Golam M Shameem
(74) *Attorney, Agent, or Firm* — CBM Patent Consulting, LLC

(57) ABSTRACT

A sulfonamide benzamide derivative has the structure shown in Formula II that can be prepared as an anti-HBV (hepatitis B virus) pharmaceutical composition; it is prepared by sulfonation reaction, acylation reaction and sulfonylation reaction; the sulfonamide benzamide derivative has been shown effective activity for anti-HBV by inhibiting HBV DNA replication in vitro.

4 Claims, No Drawings

SULFONAMIDE BENZAMIDE DERIVATIVE AND PREPARATION METHOD AND APPLICATION THEREOF

CROSS REFERENCES

This application claims priority to Chinese Patent Application Ser. No. CN 202110542168.5 filed on 18 May 2021.

TECHNICAL FIELD

The invention belongs to the field of medicinal chemistry and relates to sulfanilamide derivatives with anti-hepatitis B virus (HBV) activity and their preparation methods.

BACKGROUND OF THE INVENTION

Chronic hepatitis B virus (HBV) infection is a major global public health problem. It is estimated that about 350 million people are chronically infected with HBV worldwide, including about 93 million people in China, and about 1 million people die each year from HBV infection and its associated liver disease. Currently available drugs against HBV infection mainly include epidemic modulators and nucleoside analogues. Although these drugs can significantly inhibit HBV DNA replication, the hepatitis B virus is prone to develop resistance to them, therefore, functional cure cannot be achieved. Therefore, the discovery and development of anti-HBV drugs with novel mechanisms of action has been a hot research topic in this field for many years.

The core protein, the main structural protein of HBV capsid nucleosome, is relatively conserved during viral evolution, and the assembly of the core protein plays an important role in the hepatitis B virus life cycle. However, no drugs with relevant targets is currently on the market. In response to the shortcomings of strong hepatotoxicity, poor water solubility and poor metabolic stability of current drug candidates entering the clinic, a novel class of sulfobenzenecarboxamide compounds was designed by target-based rational drug design through the crystal complex structure of core protein and ligand.

SUMMARY OF THE INVENTION

In order to overcome the above-mentioned shortcomings of the prior compounds, the present invention provides a sulfobenzenecarboxamide derivative and its preparation method, and the present invention also provides the results of activity screening of the above compounds as non-nucleoside HBV inhibitors and their application.

The technical solutions of the present invention are as follows.

1. Sulfanilamide Benzamide Derivatives

The sulfanilamide benzamide derivative covered by the invention has the structure shown in general formula II as follows.

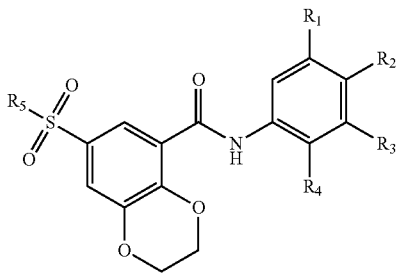

wherein $R_1$-$R_4$ are each independently selected from hydrogen or halogen; $R_5$ represents

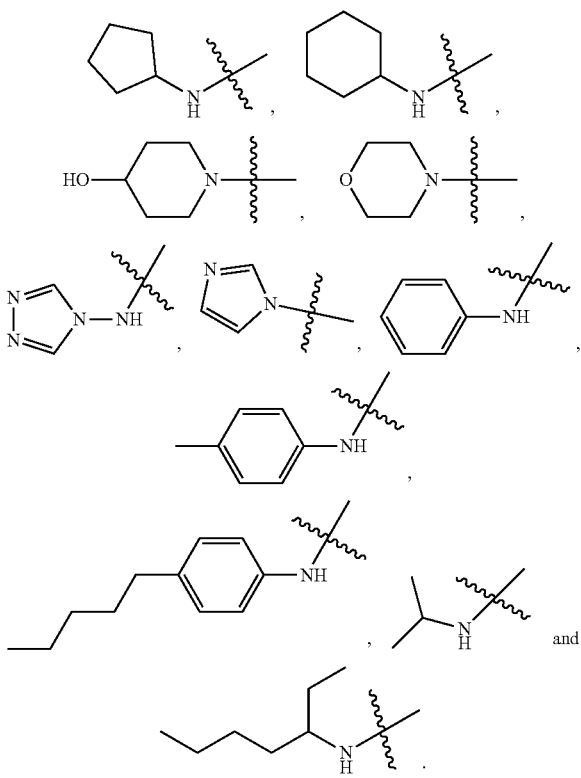

The Sulfanilamide Derivative, Characterized as One of the Following Compounds.

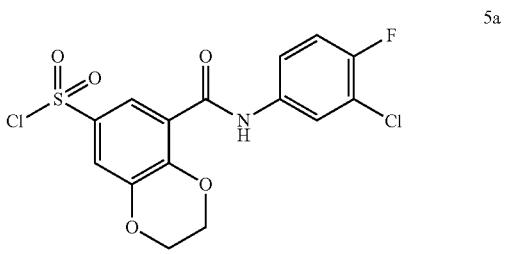

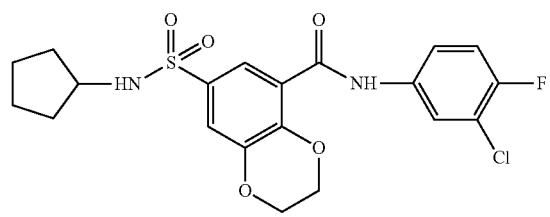
5b
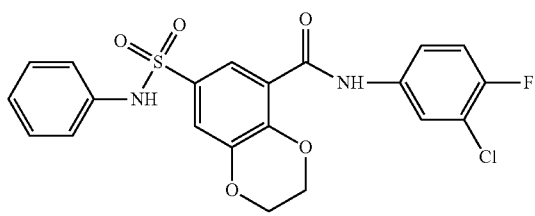
5h
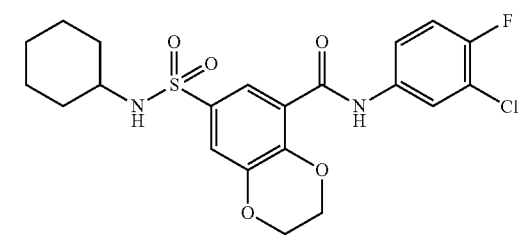
5c
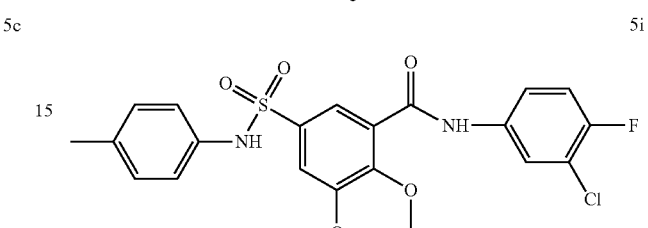
5i
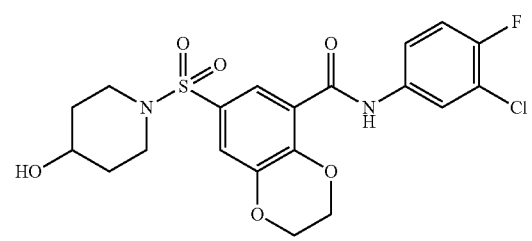
5d
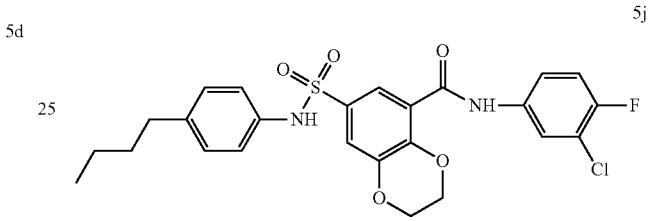
5j
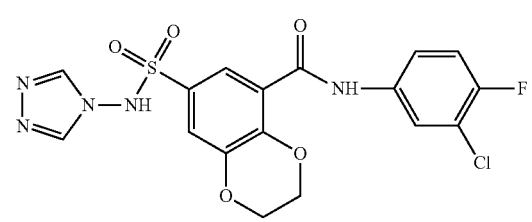
5e
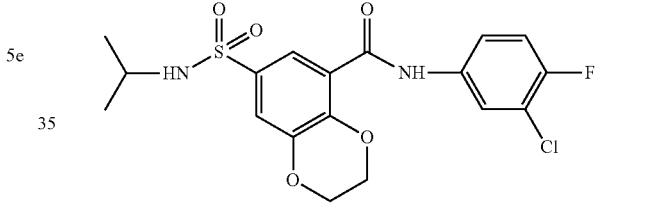
5k
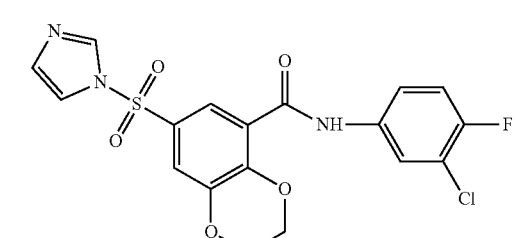
5f
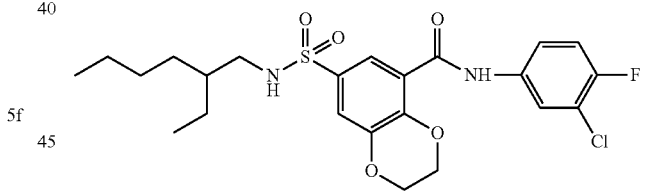
5l
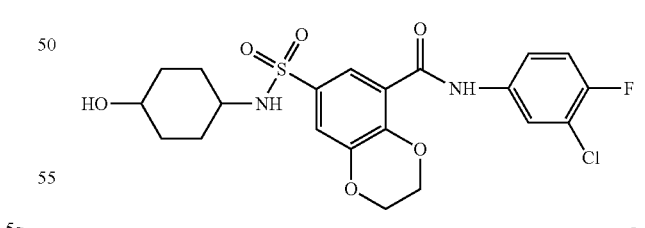
5m
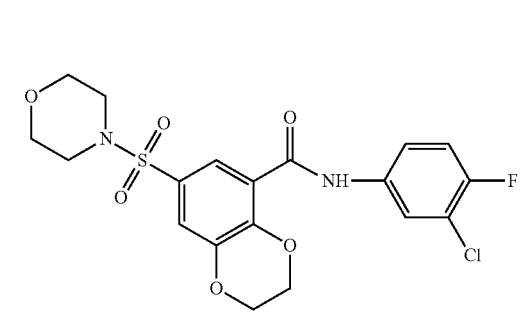
5g
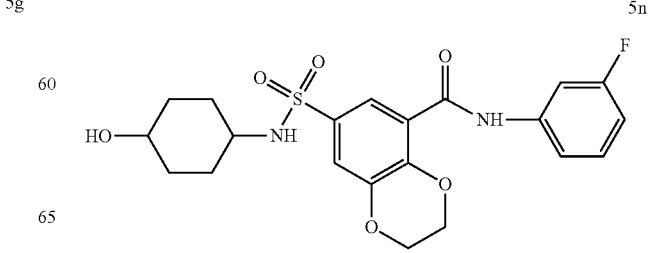
5n

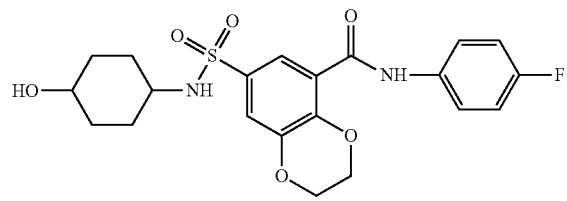

5o

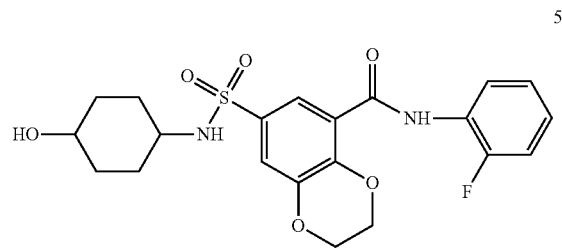

5p

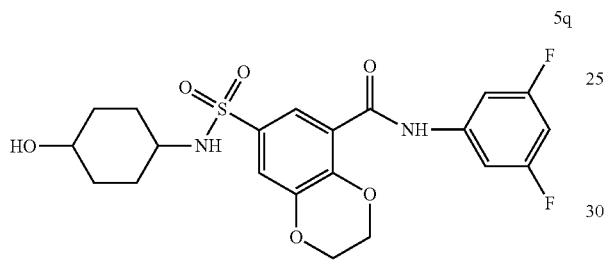

5q

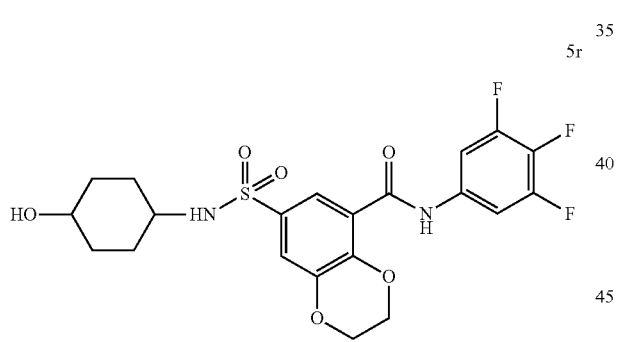

5r

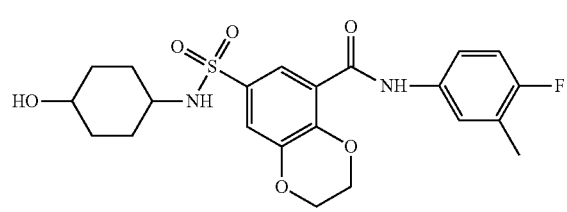

5s

2. The Preparation Methods of Sulfonamide Benzamide Derivatives

The preparation methods of sulfonamide benzamide derivatives, use 1,4-benzodioxol-6-carboxylic acid as raw material, after sulfonation reaction, acylation reaction, sulfonylation reaction, and obtain product II.

The reaction route is as follows:

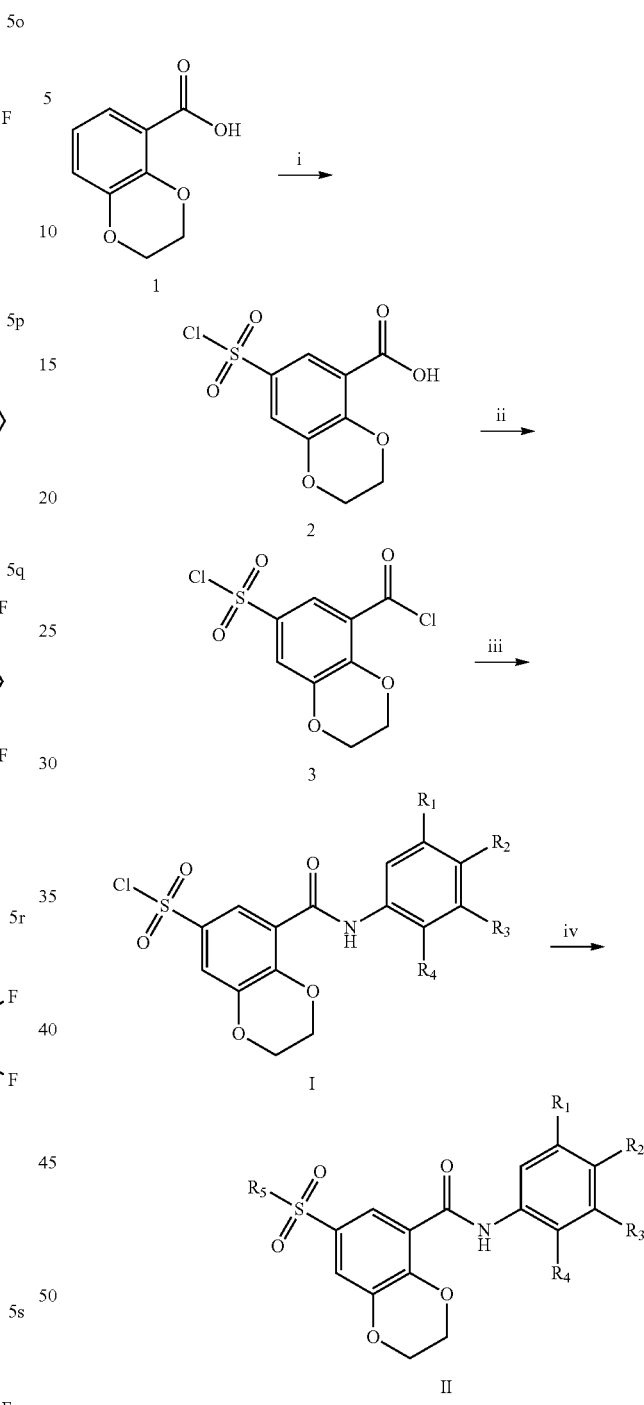

wherein $R_1$, $R_2$, $R_3$, $R_4$, $R_5$ are as described in general Formula II.

Reagents and conditions: (i) chlorosulfonic acid starting at 0° C., then increasing to 140-150° C. for 6-12 hours; (ii) chlorosulfoxide, N, N-dimethylformamide, 3-5 h, at 80° C. for 3-5 hours; (iii) acetonitrile, different types of aniline, at 60° C. for 8 hours; (iv) dichloromethane, N, N-diisopropylethylamine, different types of amines, at 45° C. for 8 hours.

The different types of aniline are selected from: 3-chloro-4-fluoroaniline, 3-fluoroaniline, 4-fluoroaniline, o-fluoroaniline, 3,5-difluoroaniline, 3,4,5-trifluoroaniline, 3-fluoro-4-methylaniline.

The different types of amines mentioned are selected from cyclohexylamine, cyclopentylamine, 4-hydroxypiperidine, 4-amino-1,2,4-triazole, imidazole, morpholine, aniline, p-methylaniline, 4-butylaniline, isopropylamine, or 2-ethylhexylamine.

The specific steps of preparation methods of sulfonamide benzamide derivatives are as follows.

(1) 18 mL, 277.54 mmol chlorosulfonic acid cool down to 0° C., slowly add 5.0032 g, 27.75 mmol 1,4-benzodioxane-6-carboxylic acid at low temperature, raise to room temperature, reflux reaction at 100° C. for 6 h; cool down to room temperature at the end of the reaction, add 150 mL ice water drop by drop, extract, wash with water and dry to obtain compound 2.

(2) Dissolve 1 g, 3.58 mmol intermediate 2 in 10 mL thionyl chloride, add 2 drops of N, N-dimethylformamide, reflux reaction at 80° C., cool to room temperature after reaction, spin evaporation to obtain intermediate 3.

(3) Dissolve intermediate 3 in 20 mL acetonitrile, add different types of aniline, reflux reaction at 60° C., cool to room temperature at the end of the reaction, concentrate, add sample by dry method, after fast preparative silica gel column separation, dichloromethane-n-hexane mixed solvent recrystallization to obtain compounds I. Anilines are selected from 3-chloro-4-fluoroaniline, 3-fluoroaniline, 4-fluoroaniline, o-fluoroaniline, 3,5-difluoroaniline, 3,4,5-trifluoroaniline, 3-fluoro-4-methylaniline.

(4) Dissolve compound I in dichloromethane, add different types of amines, add 3 times equivalent of N, N-diisopropylethylamine, reflux reaction at 45° C., after the reaction, cool to room temperature, remove dichloromethane by spin evaporation, add water, use ethyl acetate for extraction, combine organic phase, extraction with saturated salt water three times, dry by using anhydrous sodium sulfate, concentrate, add sample by dry method, after fast preparation silica gel chromatography column separation and recrystallization, the target compounds were obtained. Different types of amines are selected from cyclohexylamine, cyclopentylamine, hydroxypiperidine, morpholine, imidazole, 4-amino-1,2,4-triazole, aniline, p-methylaniline, 4-butylaniline, isopropylamine or 2-ethylhexylamine.

3. Application of Sulfobenzenecarboxamide Derivatives

The invention discloses the screening results of anti-HBV activity of sulfanilamide derivatives and their application as anti-HBV inhibitors. It was demonstrated experimentally that the sulfanilamide derivatives of the invention can be applied as classical HBV non-nucleoside inhibitors.

The anti-HBV activity of the synthesized target compounds II (5b-5s) was evaluated in vitro, and the mortality of cells at 10 μM drug concentration was determined by CCK-8 assay; Meanwhile, the inhibition of HBV DNA replication activity at 1 μL drug concentration was determined by quantitative PCR, and the lead compound 5a and the marketed drug entecavir were selected as positive controls, where 5b, 5c and 5k exhibited good HBV DNA replication inhibitory activity.

As shown in Table 1, the anti-HBV activity of the target compounds 5b, 5c and 5j was further evaluated in vitro based on the results of the initial screening, and the cytotoxicity of the drugs at different concentrations was determined by CCK-8 assay; and the inhibition of HBV DNA replication activity at different concentrations was determined by PCR. The lead compound 5a and marketed drug entecavir were selected as positive controls, and five concentration gradients (10 μM, 2 μM, 0.4 μM, 0.08 μM and 0.012 μM) were set for each compound, and the half inhibition concentration $CC_{50}$, $IC_{50}$ and selectivity coefficient (SI) were calculated, respectively.

The sulfanilamide derivatives of the invention are structurally novel non-nucleoside HBV inhibitors that can be used as lead compounds against HBV.

The sulfobenzenecarboxamide derivatives of the invention can be applied as non-nucleoside HBV inhibitors, specifically as HBV inhibitors used to synthesize anti-hepatitis B drugs.

An anti-HBV pharmaceutical composition comprising a sulfobenzenecarboxamide derivative of the invention and one or more pharmaceutically acceptable carriers or excipients.

The invention discloses such sulfobenzenecarboxamide derivatives, their synthesis methods, results of anti-HBV activity screening and their first application as anti-HBV inhibitors, and the experiments prove that sulfobenzenecarboxamide derivatives can be used as HBV inhibitors in the synthesis of anti-hepatitis B drugs.

SPECIFIC EMBODIMENTS

The following examples facilitate the understanding of the invention, but do not limit the content of the invention, and in the following examples, all the target compounds are numbered as above.

Synthetic Route:

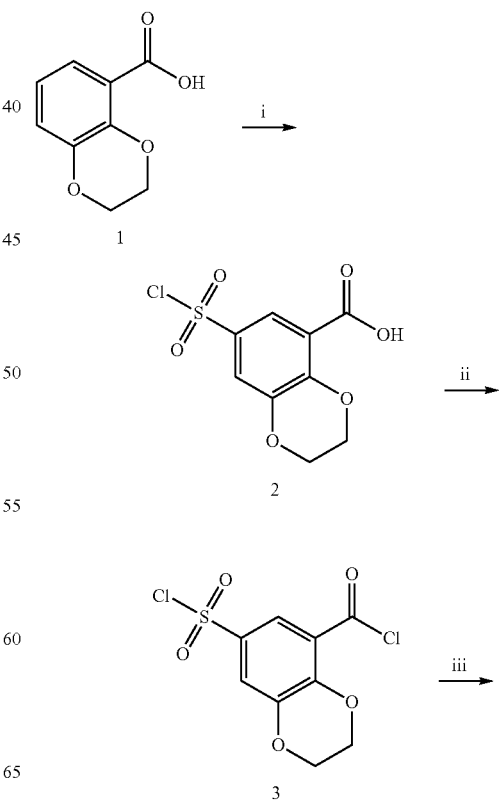

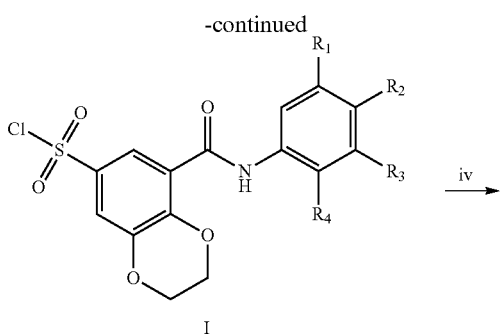

I

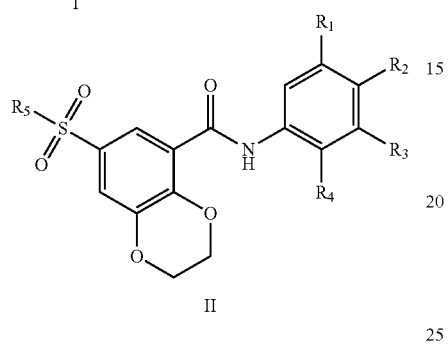

II

Reagents and conditions: (i) chlorosulfonic acid, 0° C., 6-12 h, 140-150° C.; (ii) chlorosulfoxide, N, N-dimethylformamide, 3-5h, 80° C.; (iii) acetonitrile, different types of aniline, 8 h, 60° C.; (iv) dichloromethane, N, N-disopropylethylamine, different types of amines, 8 h, 45° C.

Example 1: Preparation of Compound 2

Take a 50 mL round bottom flask, add chlorosulfonic acid (18 mL, 277.54 mmol) and cool to 0° C. Slowly add 1, 4-benzodioxole-6-carboxylic acid (5.0032 g, 27.75 mmol) at low temperature, bring to room temperature, reflux at 100° C. for 6h. After reaction, cool to room temperature, add to 150 mL chilled water drop by drop, filtered, washed with water and dry to obtain 7.0040 g of brown solid in 90.6% yield.

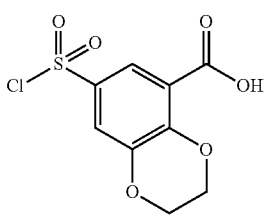

2

NMR and MS Data of Compound 2

$^1$H-NMR (400 MHz, DMSO) δ 12.54 (s, 4H), 7.52 (d, J=1.6 Hz, 1H), 7.18 (d, J=2.0 Hz, 1H), 4.31 (d, J=4.0 Hz, 2H), 4.28 (d, J=4.8 Hz, 2H).

$^{13}$C-NMR (100 MHz, DMSO) δ166.63, 144.15, 143.44, 140.33, 120.71, 120.59, 117.91, 64.73, 64.12.

ESI-MS: calculated for $C_9H_7ClO_6S$ [M−H]$^-$ 277.96519, found 276.95691.

Example 2: Preparation of Compound 3

Take a 25 ml round bottom flask, dissolve intermediate 2 (1 g, 3.58 mmol) in 10 ml sulfoxide chloride, add 2 drops of N, N-dimethylformamide, reflux reaction at 80° C., cool to room temperature after reaction, spin evaporation to obtain 1.17 g of yellow oil product.

Example 3: Preparation of Compound I

Take a 100 mL round bottom flask, dissolve intermediate 3 in 20 mL acetonitrile, add different types of aniline, reflux reaction at 60° C., cool to room temperature after reaction, concentrate, add sample by dry method, fast prepare silica gel column for separation, dichloromethane-n-hexane solvent mixture recrystallization.

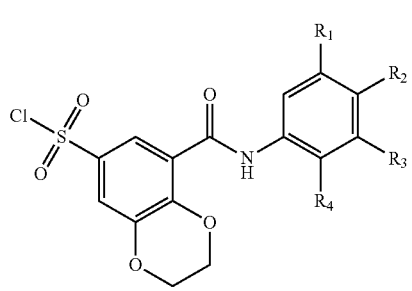

I

Example 4: Preparation of Compound 5a

Take a 100 ml round bottom flask, dissolve intermediate 3 (1 g, 3.37 mmol) in 20 mL acetonitrile, add 3-chloro-4-fluoroaniline (0.5886 g, 3.37 mmol), reflux reaction at 60° C., cool to room temperature after reaction, concentrate and add sample by dry method, fast preparation silica gel column separation, dichloromethane-n-hexane solvent mixture recrystallization, 1.0969 g yellow solid was obtained in 91% yield.

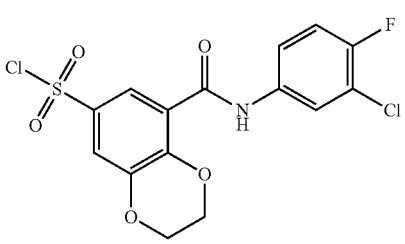

5a

NMR and MS Data of Compound 5a $^1$H-NMR (400 MHz, DMSO) δ 10.32 (s, 1H), 8.14-7.93 (m, 1H), 7.79-7.58 (m, 1H), 7.38 (dt, J=8.8, 1.2 Hz, 2H), 7.17 (d, J=2.0 Hz, 1H), 4.33 (dd, J=27.6, 3.1 Hz, 4H).

$^{13}$C-NMR (100 MHz, DMSO) δ 164.24 (d, J=11 Hz), 153.97 (d, J=201 Hz), 143.22, 141.98, 141.18, 136.54 (dd, J=11.3 Hz), 124.48 (d, J=9 Hz), 121.58 (d, J=9 Hz), 120.53 (t, J=8 Hz), 119.16, 117.44, 117.22, 116.94 (d, J=3 Hz), 65.10, 64.26.

ESI-MS: calculated for $C_{15}H_{10}C_{12}FNO_5S$[M−H]$^-$ 404.96408, found 403.95554.

Example 5: Preparation of Compound 5b

Take a 25 mL round bottom flask, dissolve intermediate 5a (720 mg, 1.7 mmol) in 10 ml dichloromethane, add cyclopentylamine (156 μL, 1.7 mmol) N, N-diisopropylethylamine (570 μL, 5.1 mmol), and reflux at 40° C. After combing the organic phases, wash with saturated salt water (20 mL×3), dry over anhydrous sodium sulfate, concentrate, add sample by dry method, separate on a silica gel column by rapid preparative chromatography and recrystallize in a dichloromethane-n-hexane solvent mixture to obtain 0.21 g white solid powder in 27% yield with a melting point of 176.6-178.1° C.

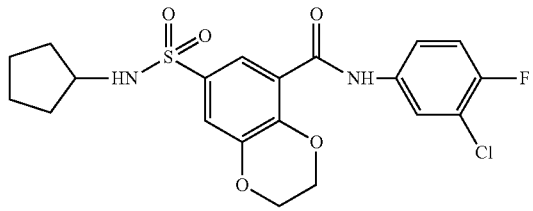

5b

NMR and MS Data of Compound 5b $^1$H-NMR (400 MHz, DMSO) δ 10.43 (s, 1H), 8.02 (dd, J=6.7, 2.2 Hz, 1H), 7.71-7.53 (m, 3H), 7.48-7.32 (m, 2H), 4.42 (dd, J=30.3, 3.0 Hz, 4H), 2.05-0.93 (m, 9H).

$^{13}$C-NMR (100 MHz, DMSO) δ 163.37, 153.93 (d, J=242 Hz), 144.75, 144.22, 136.35 (d, J=3 Hz), 134.24, 125.68, 121.70, 120.65 (d, J=7 Hz), 120.28, 119.77, 119.59, 117.48 (d, J=12 Hz), 65.37, 64.35, 54.94, 32.97, 23.28.

ESI-MS: calculated for $C_{20}H_{20}ClFN_2O_5S[M-H]^-$ 455.08215, found 454.07655.

Example 6: Preparation of Compound 5c

Take a 25 mL round bottom flask, dissolve compound 5a (300 mg, 0.7 mmol) in 10 mL dichloromethane, add cyclohexylamine (70 μL, 0.7 mmol) N, N-diisopropylethylamine (330 μL, 2.1 mmol), reflux reaction at 40° C. After the reaction cooled to room temperature, remove dichloromethane by spin evaporation, add water (40 mL) and extract by using ethyl acetate three times (20 mL×3), combine the organic phases, wash with saturated salt water (20 mL×3), dry with anhydrous sodium sulfate, concentrate and dichloromethane-n-hexane solvent mixture is recrystallized to obtain 0.18 g white solid powder, yield 54%, melting point 167.8-168.8° C.

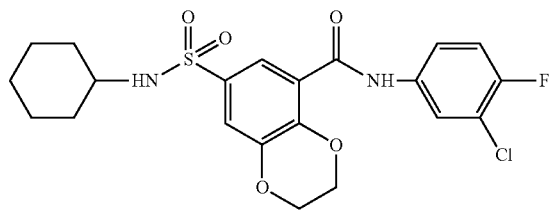

5c

NMR and MS Data of Compound 5c $^1$H-NMR (400 MHz, DMSO) δ 10.43 (s, 1H), 8.02 (dd, J=6.7, 2.0 Hz, 1H), 7.65 (d, J=6.8 Hz, 2H), 7.57 (d, J=1.6 Hz, 1H), 7.50-7.36 (m, 2H), 4.99-3.92 (m, 4H), 2.93 (s, 1H), 1.60 (d, J=7.8 Hz, 4H), 1.37-0.96 (m, 6H).

$^{13}$C-NMR (100 MHz, DMSO) δ 163.26, 153.68 (d, J=232 Hz), 144.66, 144.19, 136.36 (d, J=4 Hz), 135.05, 125.64, 120.64 (d, J=7 Hz), 120.00, 119.77, 119.59, 117.60, 117.32 (d, J=14 Hz), 65.35, 64.35, 52.61, 33.68, 25.33, 24.76.

ESI-MS: calculated for $C_{21}H_{22}ClFN_2O_5S$ $[M-H]^-$ 468.09220, found 467.08401.

Example 7: Preparation of Compound 5d

Same operation as example 5, except that cyclopentylamine was replaced with 4-hydroxypiperidine. White solid powder, yield 50%, melting point 174.6-181.3° C.

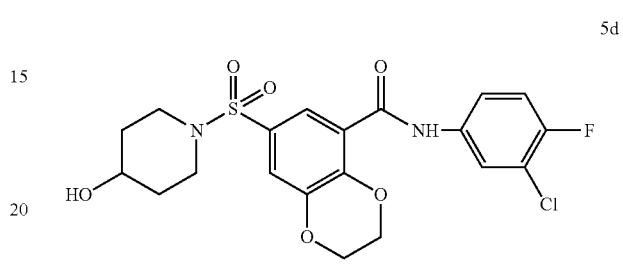

5d

NMR and MS data of compound 5d $^1$H-NMR (400 MHz, DMSO) δ 10.48 (s, 1H), 8.02 (dd, J=6.8, 2.5 Hz, 1H), 7.78-7.58 (m, 1H), 7.55-7.38 (m, 2H), 7.31 (d, J=2.1 Hz, 1H), 4.70 (d, J=3.7 Hz, 1H), 4.43 (dd, J=29.6, 3.0 Hz, 4H), 3.56 (dd, J=7.0, 3.5 Hz, 1H), 3.22-3.00 (m, 2H), 2.78 (t, J=8.1 Hz, 2H), 1.96-1.68 (m, 2H), 1.62-1.29 (m, 2H).

$^{13}$C-NMR (100 MHz, DMSO) δ 163.26, 144.92 (d, J=102 Hz), 136.36, 128.06, 126.15, 121.69, 120.95, 120.63 (d, J=7 Hz), 119.77, 119.59, 118.26, 117.61, 117.40, 65.39, 64.36, 64.05, 43.55, 33.28.

ESI-MS: calculated for $C_{20}H_{20}ClFN_2O_6S[M-H]^-$ 470.07146, found 469.06342.

Example 8: Preparation of Compound 5e

The operation was the same as in example 5, except that cyclopentylamine was replaced with 4-amino-1,2,4-triazole, and the product was a brown solid in 18% yield with a melting point of 252.1-253.2° C.

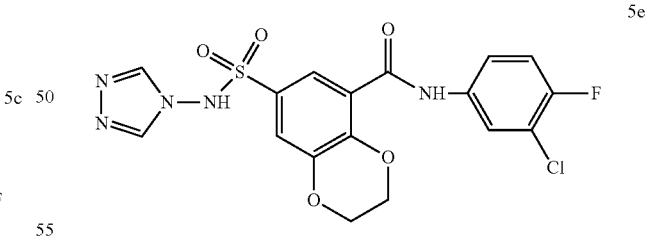

5e

NMR and MS Data of Compound 5e $^1$H-NMR (400 MHz, DMSO) δ 10.44 (s, 1H), 8.00 (dd, J=6.8, 2.4 Hz, 1H), 7.66-7.59 (m, 1H), 7.55 (t, J=8.9 Hz, 1H), 7.50 (d, J=2.3 Hz, 1H), 7.47-7.38 (m, 3H), 7.30-6.88 (m, 1H), 4.48 (d, J=41.6 Hz, 4H).

$^{13}$C-NMR (100 MHz, DMSO) δ 162.57, 154.44 (d, J=243 Hz), 152.80, 147.18, 144.52, 136.12, (d, J=3 Hz), 133.96, 132.76, 129.80, 126.04, 122.15, 121.82, 120.72 (d, J=7 Hz), 119.79, 118.99, 117.34, 65.72, 65.34.

ESI-MS: calculated for $C_{17}H_{13}ClFN_5O_5S[M+H]^+$ 453.03100, found 453.98334.

Example 9: Preparation of Compound 5f

The operation was the same as example 5, except that cyclopentylamine was replaced with imidazole and the product was a white solid with a yield of 22% and a melting point of 220.9-222.8° C.

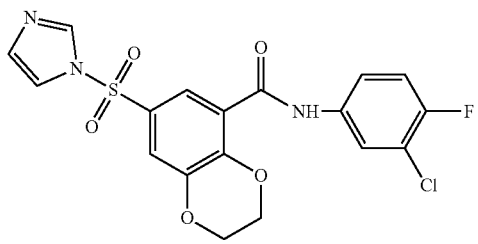

5f

NMR and MS Data of Compound 5f $^1$H-NMR (400 MHz, DMSO) δ 10.54 (s, 1H), 8.41 (s, 1H), 7.99 (dd, J=6.8, 2.3 Hz, 1H), 7.88-7.81 (m, 2H), 7.77 (d, J=2.2 Hz, 1H), 7.66-7.56 (m, 1H), 7.43 (t, J=9.1 Hz, 1H), 7.13 (s, 1H), 4.42 (dd, J=28.5, 3.2 Hz, 4H).

$^{13}$C-NMR (100 MHz, DMSO) δ 162.76, 153.98 (d, J=242 Hz), 147.28, 144.92, 137.77, 136.21, (d, J=3 Hz), 131.67, 129.27, 127.01, 121.09, 120.55 (d, J=7 Hz), 119.83, 118.79, 117.93, 117.67, 117.45, 65.57, 64.36.

ESI-MS: calculated for $C_{18}H_{13}ClFN_3O_5S[M-H]^-$ 437.02485, found 436.01538.

Example 10: Preparation of Compound 5g

The operation was the same as example 5, except that the cyclopentylamine was replaced with morpholine group and the product was a white solid, yield 78.7%, melting point 249.5-252.2° C.

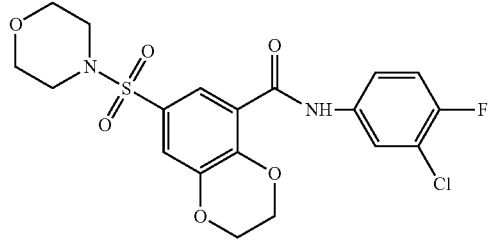

5g

NMR and MS Data of Compound 5g.

$^1$H-NMR (400 MHz, DMSO) δ 10.39 (s, 1H), 10.14 (s, 1H), 7.99 (dd, J=6.8, 2.3 Hz, 1H), 7.66-7.57 (m, 1H), 7.53 (d, J=2.0 Hz, 1H), 7.42 (t, J=9.1 Hz, 1H), 7.32 (d, J=2.0 Hz, 1H), 7.03 (q, J=8.4 Hz, 4H), 4.38 (dd, J=32.7, 2.9 Hz, 4H), 2.19 (s, 3H).

$^{13}$C-NMR (100 MHz, DMSO) δ 163.22, 154.16 (d, J=253 Hz), 145.73, 144.51, 137.77, 136.35 (d, J=2.9 Hz), 126.78, 126.30, 121.69, 121.13, 120.63 (d, J=7.0 Hz), 119.68 (d, J=18.5 Hz), 118.45, 117.60, 117.39, 65.72, 65.4.

ESI-MS: calculated for $C_{19}H_{18}ClFN_2O_6S[M-H]^-$ 456.05581, found 455.04691.

Example 11: Preparation of Compound 5h

The operation was the same as example 5, except that cyclopentylamine was replaced with aniline and the product was a white solid with a yield of 41% and a melting point of 223.0-226.8° C.

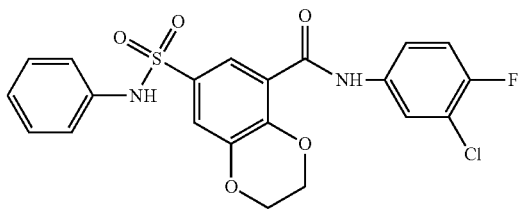

5h

NMR and MS Data of Compound 5h $^1$H-NMR (400 MHz, DMSO) δ 10.41 (t, J=47.3 Hz, 2H), 7.98 (d, J=6.8 Hz, 1H), 7.69-7.49 (m, 2H), 7.45-7.31 (m, 3H), 7.30-7.20 (m, 1H), 7.19-7.09 (m, 1H), 7.03 (t, J=7.3 Hz, 1H), 4.38 (d, J=33.2 Hz, 4H).

$^{13}$C-NMR (100 MHz, DMSO) δ 163.04 (d, J=9.9 Hz), 154.53 (d, J=242.1 Hz), 136.25, 131.58, 129.76, 125.86 (d, J=10.5 Hz), 124.54, 122.02, 121.68 (d, J=5.2 Hz), 120.98-120.08, 119.70 (d, J=18.5 Hz), 118.02, 117.50 (dd, J=14.9, 6.8 Hz), 65.41, 64.31.

ESI-MS: calculated for $C_{21}H_{16}ClFN_2O_5S[M-H]^-$ 462.04525, found 461.03491.

Example 12: Preparation of Compound 5i

The operation was the same as example 5, except that cyclopentylamine was replaced with p-methylaniline and the product was a white solid with a yield of 70% and a melting point of 229.1-237.0° C.

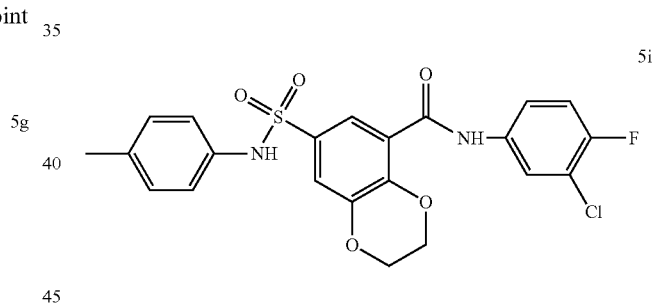

5i

NMR and MS Data of Compound 5i $^1$H-NMR (400 MHz, DMSO) δ 10.39 (s, 1H), 10.14 (s, 1H), 7.99 (dd, J=6.8, 2.3 Hz, 1H), 7.66-7.57 (m, 1H), 7.53 (d, J=2.0 Hz, 1H), 7.42 (t, J=9.1 Hz, 1H), 7.32 (d, J=2.0 Hz, 1H), 7.03 (q, J=8.4 Hz, 4H), 4.38 (dd, J=32.7, 2.9 Hz, 4H), 2.19 (s, 3H).

$^{13}$C-NMR (100 MHz, DMSO) δ 163.11, 153.95 (d, J=242 Hz), 145.24, 144.20, 136.25, 135.41, 133.83, 132.29, 130.16, 125.73, 121.68, 120.70, 120.59, 120.51, 119.70 (d, J=18.3 Hz), 117.58 (d, J=18.3 Hz), 117.38, 65.36, 64.30, 20.75.

ESI-MS: calculated for $C_{22}H_{18}ClFN_2O_5S[M-H]^-$ 476.06090, found 475.05130.

Example 13: Preparation of Compound 5j

The product was prepared as in example 5, except that cyclopentylamine was replaced with 4-butylaniline and the product was a white solid with a yield of 75% and a melting point of 168.9-171.9° C.

NMR and MS Data of Compound 5j

¹H-NMR (400 MHz, DMSO) δ 10.38 (s, 1H), 10.14 (s, 1H), 7.99 (d, J=4.8 Hz, 1H), 7.64-7.57 (m, 1H), 7.51 (s, 1H), 7.41 (t, J=9.1 Hz, 1H), 7.32 (d, J=1.3 Hz, 1H), 7.05 (dd, J=19.2, 8.3 Hz, 4H), 4.59-4.13 (m, 4H), 2.46 (t, J=7.6 Hz, 2H), 1.58-1.37 (m, 2H), 1.24 (dd, J=14.6, 7.3 Hz, 2H), 0.84 (t, J=7.3 Hz, 3H).

¹³C-NMR (101 MHz, DMSO) δ 163.10, 153.94 (d, J=242 Hz), 145.23, 144.20, 138.78, 136.29, 135.59, 132.37, 129.47, 125.73, 121.66, 120.73, 120.6, 120.56, 120.43, 119.69 (d, J=18.4 Hz), 117.5 (d, J=6 Hz), 117.37, 65.36, 64.30, 34.54, 33.51, 22.15, 14.19.

ESI-MS: calculated for $C_{26}H_{26}ClFN_2O_5S[M-H]^-$ 518.10785, found 517.09808.

Example 14: Preparation of Compound 5k

The product was prepared as in example 5, except that cyclopentylamine was replaced with isopropylamine and the product was a white solid with a yield of 66% and a melting point of 170.4-172.3° C.

NMR and MS Data of Compound 5k

¹H-NMR (400 MHz, DMSO) δ 10.43 (s, 1H), 8.02 (dd, J=6.8, 2.4 Hz, 1H), 7.76-7.51 (m, 3H), 7.51-7.34 (m, 2H), 4.42 (dd, J=29.8, 3.1 Hz, 4H), 3.23 (dd, J=13.1, 6.6 Hz, 1H), 0.98 (d, J=6.5 Hz, 6H).

¹³C-NMR (100 MHz, DMSO) δ 163.37, 154.23 (d, J=252.4 Hz), 144.71, 144.23, 135.37, 134.55, 125.71, 121.69, 120.65 (d, J=7 Hz), 120.12, 119.77, 117.61, 117.39, 111.69, 65.35, 64.36, 46.77, 23.72.

ESI-MS: calculated for $C_{18}H_{18}ClFN_2O_5S[M-H]^-$ 428.06090, found 427.05164.

Example 15: Preparation of Compound 5l

The product was prepared as in example 5, except that cyclopentylamine was replaced with 2-ethylhexylamine and the product was a white solid with a yield of 40% and a melting point of 190.9-193.7° C.

NMR and MS Data of Compound 5l

¹H-NMR (400 MHz, DMSO) δ 10.43 (s, 1H), 8.01 (d, J=5.5 Hz, 1H), 7.76-7.25 (m, 5H), 4.41 (d, J=28.9 Hz, 4H), 2.63 (s, 2H), 1.46-1.04 (m, 9H), 0.96-0.63 (m, 6H).

¹³C-NMR (100 MHz, DMSO) δ 163.37, 153.98 (d, J=246 Hz), 144.78, 144.27, 136.30, 133.37, 125.71, 121.71, 120.64, 120.21, 119.71, 119.63, 117.60, 117.43, 65.37, 64.36, 45.81, 30.62, 28.62, 23.74, 22.87, 14.39, 10.99.

ESI-MS: calculated for $C_{23}H_{28}ClFN_2O_5S[M-H]^-$ 498.13915, found 497.12875.

Example 16: Preparation of Compound 5m

The product was prepared as in example 5, except that p-hydroxycyclohexylamine was used instead of cyclopentylamine and the product was a yellow solid with a yield of 58% and a melting point of 201.1-202.4° C.

NMR and MS Data of Compound 5m

¹H-NMR (400 MHz, DMSO) δ 10.42 (s, 1H), 8.01 (dd, J=6.8, 2.4 Hz, 1H), 7.62 (m, 3H), 7.41 (dd, J=12.3, 9.2 Hz, 2H), 4.73-3.81 (m, 5H), 3.30 (d, J=9.2 Hz, 1H), 3.13-2.72 (m, 1H), 1.67 (dd, J=32.9, 11.1 Hz, 4H), 1.39-0.87 (m, 4H).

¹³C-NMR (100 MHz, DMSO) δ 163.36, 154.24 (d, J=242 Hz), 144.69, 144.21, 136.33 (d, J=3.0 Hz), 134.86, 125.66, 121.71, 120.66 (d, J=7 Hz)), 120.02, 119.78, 119.60, 117.37 (t, J=21 Hz), 68.02, 65.35, 64.34, 52.14, 33.98, 31.44.

ESI-MS: calculated for $C_{21}H_{22}ClFN_2O_6S[M-H]^-$ 484.08711, found 483.07886.

Example 17: Preparation of Compound 5n

The first operation was the same as example 4, replacing 3-chloro-4-fluoroaniline with 3-fluoroaniline, and the subsequent operation was the same as example 16, with the product being a white solid in 40% yield and a melting point of 111.1-120.1° C.

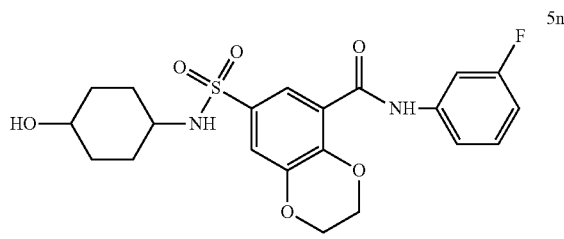 [SMILES: O=C(Nc1cccc(F)c1)c1cc(S(=O)(=O)NC2CCC(O)CC2)cc2c1OCCO2]

NMR and MS Data of Compound 5n $^1$H-NMR (400 MHz, DMSO) δ 10.43 (s, 1H) 7.70 (d, J=11.6 Hz, 1H), 7.62 (d, J=7.0 Hz, 1H), 7.56 (d, J=2.0 Hz, 1H), 7.52-7.35 (m, 3H), 6.95 (td, J=8.5, 2.2 Hz, 1H), 4.66-4.14 (m, 5H), 3.33-3.26 (m, 1H), 3.05-2.76 (m, 1H), 1.68 (dd, J=31.9, 11.5 Hz, 4H), 1.30-0.90 (m, 4H).

$^{13}$C-NMR (100 MHz, DMSO) δ 163.79, 162.44 (d, J=209 Hz), 144.66, 144.20, 140.81 (d, J=11.0 Hz), 134.85, 130.94 (d, J=9.5 Hz), 125.95, 119.96, 117.17, 116.02, 110.85 (d, J=21 Hz), 106.99 (d, J=27 Hz), 68.02, 65.33, 64.35, 55.37, 52.14, 33.98, 31.44.

ESI-MS: calculated for $C_{21}H_{23}FN_2O_6S[M-H]^-$ 450.12609, found 449.11536.

Example 18: Preparation of Compound 5o

The first operation was the same as example 4, replacing 3-chloro-4-fluoroaniline with p-fluoroaniline, the subsequent operation was the same as example 16, the product was a white solid with a yield of 42% and a melting point of 205.1-207.5° C.

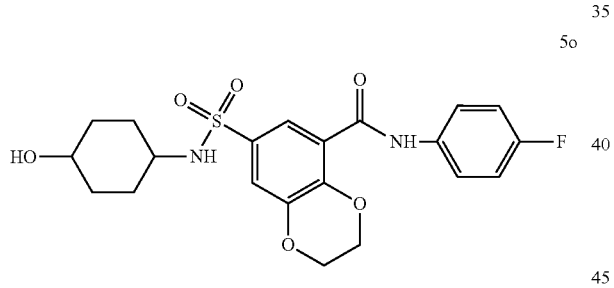

NMR and MS Data of Compound 5o $^1$H-NMR (400 MHz, DMSO) δ 10.30 (s, 1H), 7.73 (dd, J=8.1, 5.3 Hz, 2H), 7.63 (d, J=6.9 Hz, 1H), 7.55 (s, 1H), 7.38 (s, 1H), 7.21 (t, J=8.7 Hz, 2H), 4.45 (dd, J=26.2, 23.1 Hz, 5H), 3.29 (s, 1H), 2.94-2.80 (m, 1H), 1.67 (dd, J=33.1, 11.4 Hz, 4H), 1.35-0.75 (m, 4H).

$^{13}$C-NMR (100 MHz, DMSO) δ 163.07, 159.27 (d, J=333 Hz), 144.62, 144.16, 135.71, 134.76, 126.13, 122.04 (d, J=8 Hz), 119.97, 117.03, 115.99, 115.76, 68.01, 66.29, 64.39, 52.12, 33.98, 31.44.

ESI-MS: calculated for $C_{21}H_{23}FN_2O_6S[M-H]^-$ 450.12609, found 449.11542.

Example 19: Preparation of Compound 5p

The first operation was the same as example 4, replacing 3-chloro-4-fluoroaniline with o-fluoroaniline, and the subsequent operation was the same as example 16. The product was a white solid with a yield of 45% and a melting point of 200.0-200.8° C.

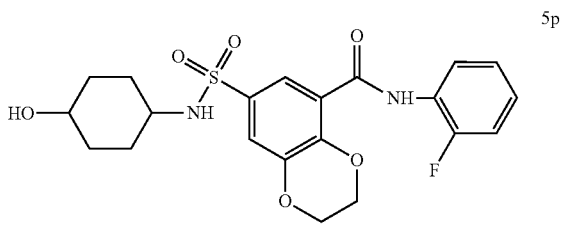 [SMILES: O=C(Nc1ccccc1F)c1cc(S(=O)(=O)NC2CCC(O)CC2)cc2c1OCCO2]

NMR and MS data of compound 5p $^1$H-NMR (400 MHz, DMSO) δ 10.06 (s, 1H), 8.04 (t, J=8.6 Hz, 1H), 7.79 (d, J=1.6 Hz, 1H), 7.65 (d, J=7.0 Hz, 1H), 7.43 (d, J=1.7 Hz, 1H), 7.38-7.28 (m, 1H), 7.27-7.17 (m, 2H), 4.47 (d, J=51.4 Hz, 5H), 3.31-3.25 (m, 1H), 2.97-2.82 (m, 1H), 1.68 (dd, J=33.1, 11.5 Hz, 4H), 1.13 (ddd, J=35.5, 17.0, 8.7 Hz, 4H).

$^{13}$C-NMR (100 MHz, DMSO) δ 162.57, 154.23 (d, J=241 Hz), 145.29, 144.37, 134.93, 126.25 (d, J=11.1 Hz), 125.03, 124.61, 123.87, 120.91, 117.87, 115.97 (d, J=19.2 Hz), 68.03, 65.67, 64.21, 52.17, 34.00, 31.44.

ESI-MS: calculated for $C_{21}H_{23}FN_2O_6S[M-H]^-$ 450.12609, found 449.12653.

Example 20: Preparation of Compound 5q

The first operation was the same as example 4, replacing 3-chloro-4-fluoroaniline with o-fluoroaniline, and the subsequent operation was the same as example 16. The product was a white solid with a yield of 45% and a melting point of 200.0-200.8° C.

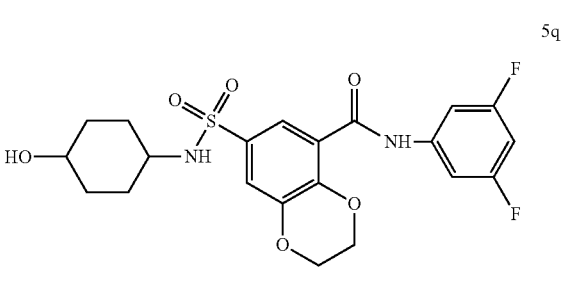 [SMILES: O=C(Nc1cc(F)cc(F)c1)c1cc(S(=O)(=O)NC2CCC(O)CC2)cc2c1OCCO2]

NMR and MS Data of Compound 5q $^1$H-NMR (400 MHz, DMSO) δ 10.59 (s, 1H), 7.63 (d, J=7.0 Hz, 1H), 7.56 (d, J=2.1 Hz, 1H), 7.46 (d, J=7.7 Hz, 2H), 7.41 (d, J=2.1 Hz, 1H), 6.98 (t, J=5.7 Hz, 1H), 4.42 (dd, J=29.4, 3.3 Hz, 5H), 3.31-3.25 (m, 1H), 3.00-2.81 (m, 1H), 1.68 (dd, J=32.7, 12.0 Hz, 4H), 1.26-0.98 (m, 4H).

$^{13}$C-NMR (100 MHz, DMSO) δ 163.77, 162.77 (d, J=199 Hz), 144.69, 144.23, 134.92, 125.58, 119.95, 117.36, 103.25, 102.96, 99.53, 68.01, 65.37, 64.36, 52.14, 33.97, 31.43.

ESI-MS: calculated for $C_{21}H_{22}F_2N_2O_6S[M-H]^-$ 468.11666, found 467.10590.

Example 21: Preparation of Compound 5r

The first operation was the same as example 4, replacing 3-chloro-4-fluoroaniline with 3,4,5-trifluoroaniline, and the subsequent operation was the same as example 16, the product was a white solid with a yield of 50% and a melting point of 225.1-228.0° C.

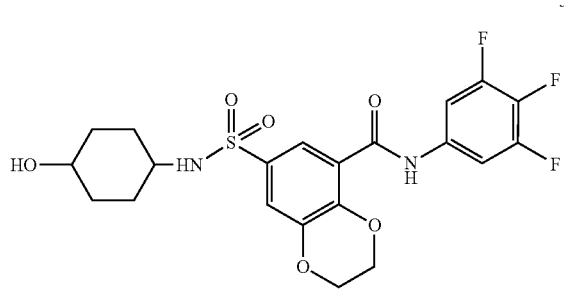

5r

NMR and MS data of compound 5r $^1$H-NMR (400 MHz, DMSO) δ 10.57 (s, 1H), 7.69-7.60 (m, 3H), 7.56 (d, J=1.9 Hz, 1H), 7.41 (d, J=1.9 Hz, 1H), 4.64-4.13 (m, 5H), 3.30 (d, J=4.2 Hz, 1H), 2.89 (s, 1H), 1.67 (dd, J=34.3, 11.6 Hz, 4H), 1.43-0.91 (m, 4H).

$^{13}$C-NMR (100 MHz, DMSO) δ 163.70, 150.65 (d, J=202 Hz), 144.69, 144.24, 134.94, 125.38, 119.95, 117.41, 104.74, 104.50, 68.01, 65.38, 64.36, 52.14, 33.97, 31.43.

ESI-MS: calculated for $C_{20}H_{21}F_3N_2O_3S$ [M−H]$^-$ 486.10724, found 485.09830.

Example 22: Preparation of Compound 5s

The first operation was the same as example 4, replacing 3-chloro-4-fluoroaniline with 3-fluoro-4-methylaniline, and the subsequent operation was the same as example 16, the product was a white solid with a yield of 42% and a melting point of 201.1-202.4° C.

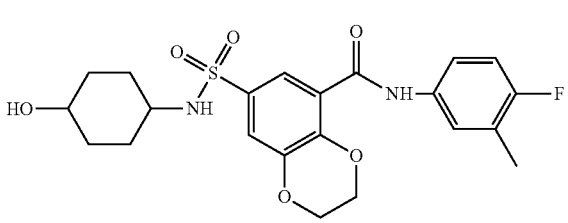

5s

NMR and MS Data of Compound 5s $^1$H-NMR (400 MHz, DMSO) δ 10.18 (s, 1H), 7.62 (d, J=6.9 Hz, 2H), 7.58-7.50 (m, 2H), 7.38 (d, J=1.7 Hz, 1H), 4.41 (dd, J=31.0, 3.2 Hz, 5H), 3.29 (dd, J=9.0, 5.0 Hz, 1H), 3.00-2.75 (m, 1H), 2.24 (s, 3H), 1.68 (dd, J=31.9, 11.7 Hz, 4H), 1.25-0.94 (m, 5H).

$^{13}$C-NMR (100 MHz, DMSO) δ 162.96, 157.43 (d, J=238 Hz), 144.65, 144.13, 135.15, 134.78, 126.07, 124.80 (d, J=18 Hz), 123.29 (d, J=5 Hz), 120.02, 119.53 (d, J=8 Hz), 117.05, 115.57, 115.34, 68.02, 65.32, 64.33, 52.14, 33.99, 31.43, 14.83.

ESI-MS: calculated for $C_{22}H_{25}FN_2O_6S$[M−H]$^-$ 464.14174, found 463.13527.

Example 23: In Vitro Anti-HBV Cellular Activity Screening Assay of Target Compounds Test Principle HBV stably transfected hepatocellular carcinoma cell line, HepAD38, was able to secrete HBV viral particles (containing HBsAg, HBeAg and DNA) when the cells were cultured. The amount of HBsAg and HBeAg secreted by the cells and the DNA produced varied under the intervention of anti-HBV target compounds, so the antiviral activity of the sample drug could be calculated by measuring the amount of HBsAg and HBeAg secreted by the cells into the culture supernatant and the HBV DNA produced, with reference to the amount in the unspiked control. Using entecavir as a positive control drug, the concentration of the drug at 50% inhibition of HBV DNA was measured by quantitative PCR at the value of $IC_{50}$; the concentration of the sample drug causing 50% cell death was measured by CCK-8 at the value of $CC_{50}$, and the "selectivity index" of the compound to be tested was calculated. $SI=CC_{50}/IC_{50}$. (1) Cytotoxicity assay Each sample was prepared with HepAD38 cell culture medium at a diluted concentration (1 μM) for preliminary activity screening, and a blank control was set up and a positive control drug was added to the 96-well cell culture plate with 3 replicate wells per concentration, and the same concentration was changed every 2 days and a drug-free cell control group was set up for 10 days. Cell viability was measured by CCK-8 assay to determine the toxicity of the drug to HepAD38 cells. Five dilutions (10 μM, 2 μM, 0.4 μM, 0.08 μM and 0.012 μM/L) were prepared in HepAD38 cell culture medium for compounds with low toxicity, and a blank control and entecavir and lead compound 5a were used as positive control drugs. Cell culture plates were added to 96-well plates with 3 replicate wells per concentration, and the same concentration was changed every 2 days and a drug-free cell control group was set up for 10 days. Cell viability was measured by CCK-8 assay to determine the toxicity of the drug on HepAD38 cells.

(2) HBV DNA Activity Inhibition Assay (Quantitative PCR Method)

HepAD38 cells were cultured in 96-well cell culture plate for 24 hours, then 10 μM, 2 μM, 0.4 μM, 0.08 μM and 0.012 μM drug-containing medium was added and the cells were incubated for 10 days (changed every 2 days), the supernatant was collected and the supernatant HBV DNA content was measured by quantitative PCR.

TABLE 1

| | Anti-hepatitis B virus activity of the active compounds and the marketed drug entecavir | | | |
|---|---|---|---|---|
| Number | $CC_{50}$ ((μM) | $EC_{50}$ (μM) | $IC_{90}$ (μM) | SI |
| 5b | >10 | 0.00252 | 0.293 | >100 |
| 5c | >10 | 0.01490 | 0.430 | >100 |
| 5k | >10 | 0.00096 | 0.099 | >100 |
| ETV | >10 | 0.000121 | 0.021 | >100 |

As shown in Table 1, further in vitro evaluation of the anti-HBV activity of initially screened target compounds 5b, 5c and 5k was performed based on the results of the initial screening, and the cytotoxicity of the drugs at different concentrations was determined by CCK-8 assay; the activity of the drugs in inhibiting HBV DNA at different concentrations was determined by quantitative PCR. Five concentration gradients (10 μM, 2 μM, 0.4 μM, 0.08 μM and 0.012 μM) were set for each compound with the listed drug entecavir as positive control, and the half inhibition concentration $CC_{50}$, $IC_{50}$ and selectivity coefficient SI were calculated, respectively.

The activity results showed that the target compounds 5b, 5c, and 5k all exhibited less cytotoxicity with $CC_{50}$>10 μM and 5k showed better anti-HBV DNA replication activity. Its IC$_{50}$ was 0.00096 μM, which is not as good as the marketed drug entecavir, but still allows for further modification studies.

What is claimed is:

1. A sulfonamide benzamide derivative having the structure shown in general formula II as follows;

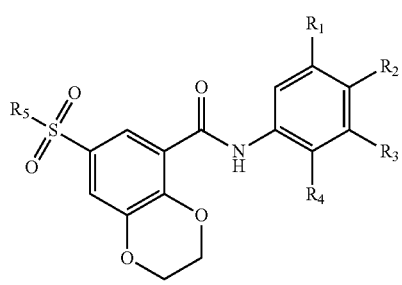

wherein R$_1$-R$_4$ are each independently selected from hydrogen or halogen; R$_5$ is selected from the group consisting of

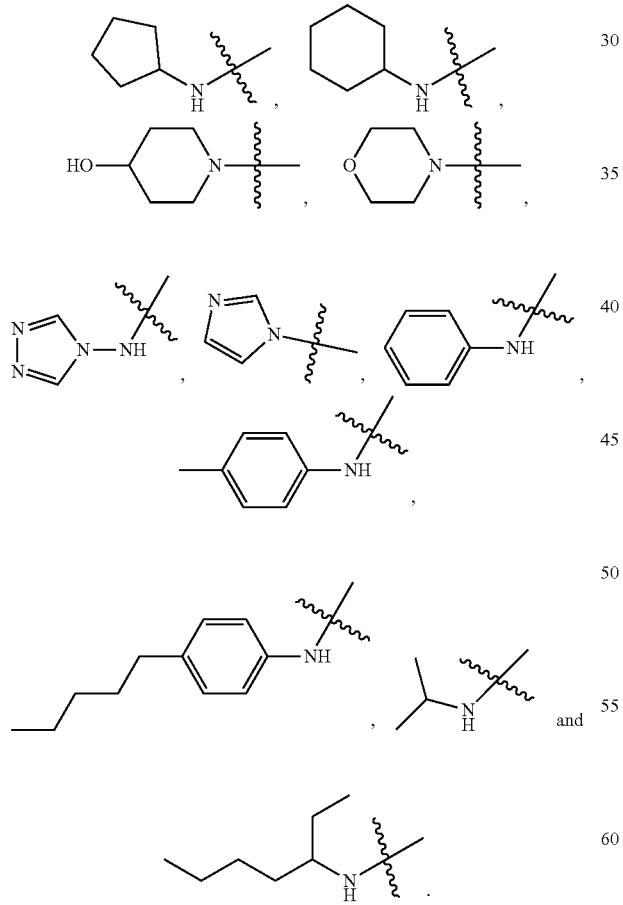

2. The sulfanilamide derivative according to claim 1, wherein the sulfanilamide derivative is selected from the group consisting of

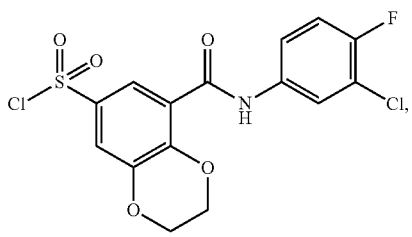

5a

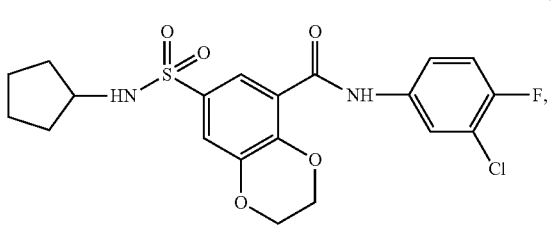

5b

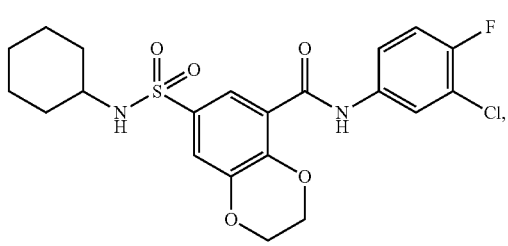

5c

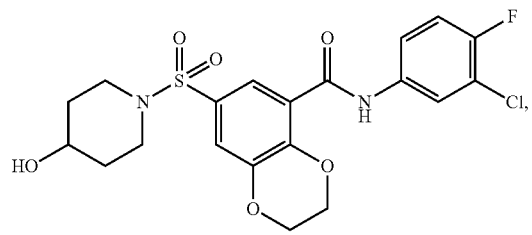

5d

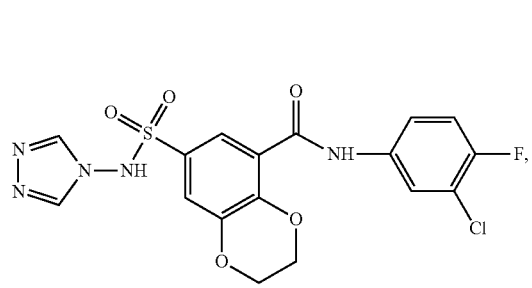

5e

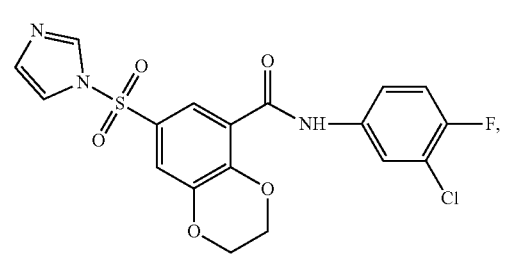

5f

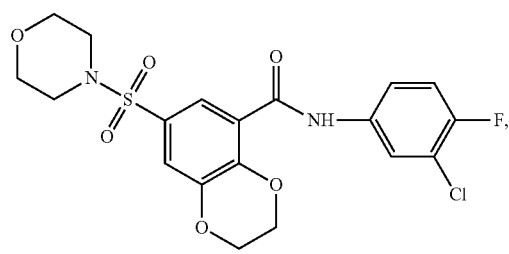
5g
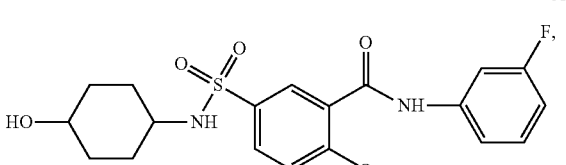
5n
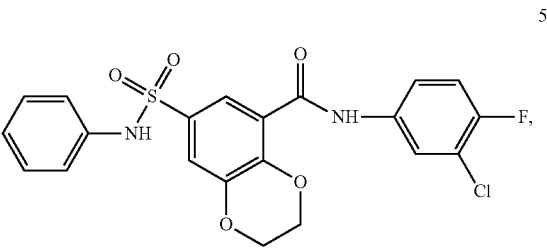
5h
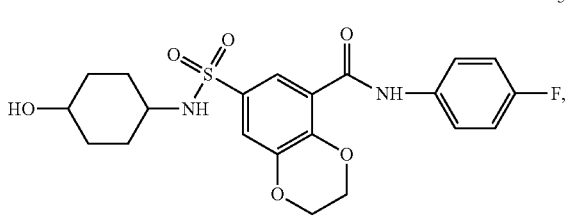
5o
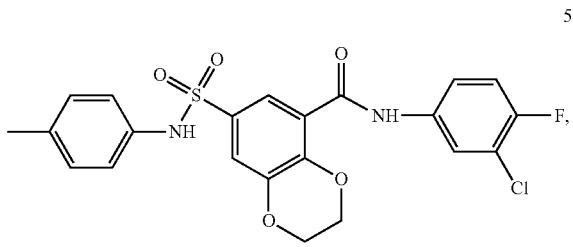
5i
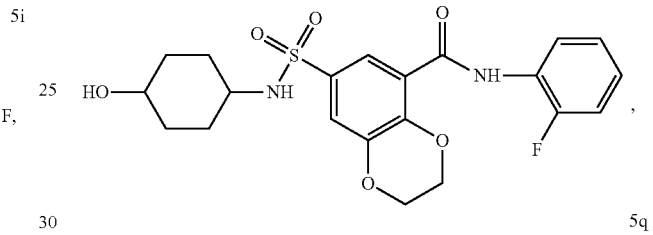
5p
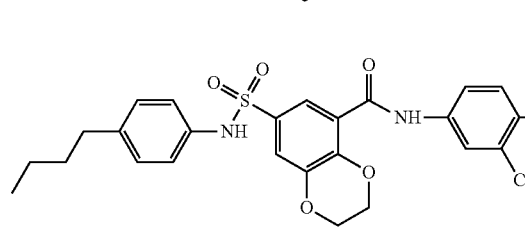
5j
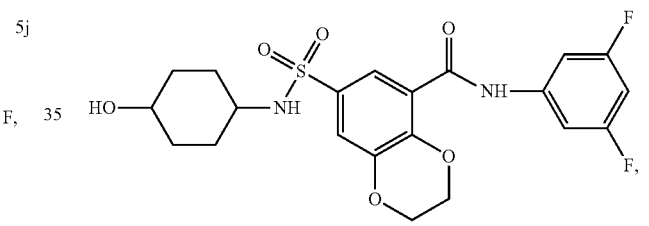
5q
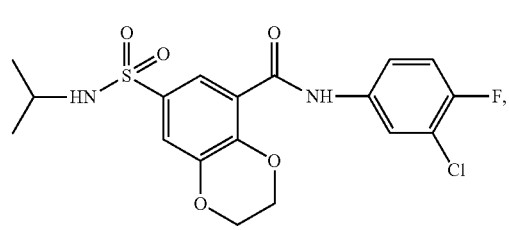
5k
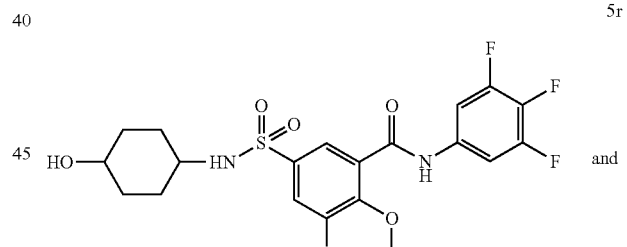
5r
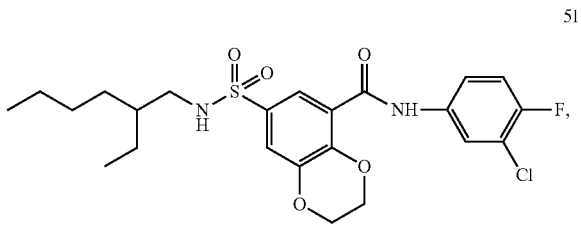
5l
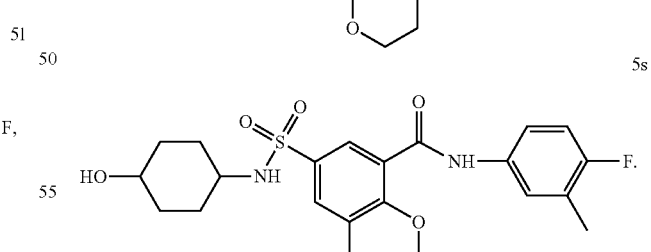
5s
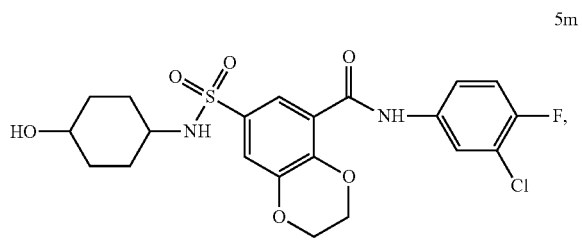
5m
3. The sulfanilamide derivative according to claim 1, wherein the sulfanilamide derivative is prepared as an anti-hepatitis B drug.
4. The sulfanilamide derivative according to claim 2, wherein the sulfanilamide derivative is prepared as an anti-hepatitis B drug.
* * * * *